United States Patent [19]

Bock et al.

[11] Patent Number: 5,037,381
[45] Date of Patent: Aug. 6, 1991

[54] ELECTRICALLY ASSISTED TRANSDERMAL TRANSPORT DEVICE AND METHOD FOR RENEWING THE DEVICE

[76] Inventors: C. Randolph Bock, 3306 Lassiter Road, Durham, N.C. 27707; Burton H. Sage, Jr., 8404 Lakewood Dr., Raleigh, N.C. 27612

[21] Appl. No.: 558,944

[22] Filed: Jul. 27, 1990

[51] Int. Cl.[5] ............................................. A61N 1/30
[52] U.S. Cl. ........................................ 604/20; 429/27; 128/803
[58] Field of Search .......... 128/803, 798, 783, 419 R; 604/20; 429/113, 27, 49

[56] References Cited

U.S. PATENT DOCUMENTS

| | | | |
|---|---|---|---|
| 4,640,689 | 2/1987 | Sibalis | 604/20 |
| 4,693,946 | 9/1987 | Niksa | 429/27 |
| 4,731,049 | 3/1988 | Parsi | 604/20 |
| 4,756,980 | 7/1988 | Niksa | 429/27 |
| 4,842,577 | 6/1989 | Konno | 604/20 |

*Primary Examiner*—William E. Kamm
*Assistant Examiner*—Robert L. Nasser, Jr.

[57] ABSTRACT

A device for electrically assisted transport of molecules into the skin has a renewable power source and a means for electrically assisted transport of molecules in solution through the skin of an animal. The device has an anode and a battery electrolyte in fluid communication in a disposable part of the means for electrically assisted transport of molecules in solution. The device has an air cathode on a reusable part of the means for electrically assisted transport so that when the reusable and disposable parts join, the battery electrolyte and the air cathode are in fluid communication. The power source is thereby renewed and electrically connected to the means for electrically assisted transport. A method for renewing and replenishing a power source for the device for electrically assisted transport of molecules in solution provides means for electrically assisted transport having a reusable part and a disposable part. The method includes providing the reusable part with an air cathode and an anode contact on a support and providing the disposable part having an anode in fluid communication with a battery electrolyte on a carrier. The method renews the power source by joining the support and the carrier. The battery electrolyte, the air cathode and the anode are thus joined in fluid communication and the anode with the anode contact are electrically connected.

19 Claims, 2 Drawing Sheets

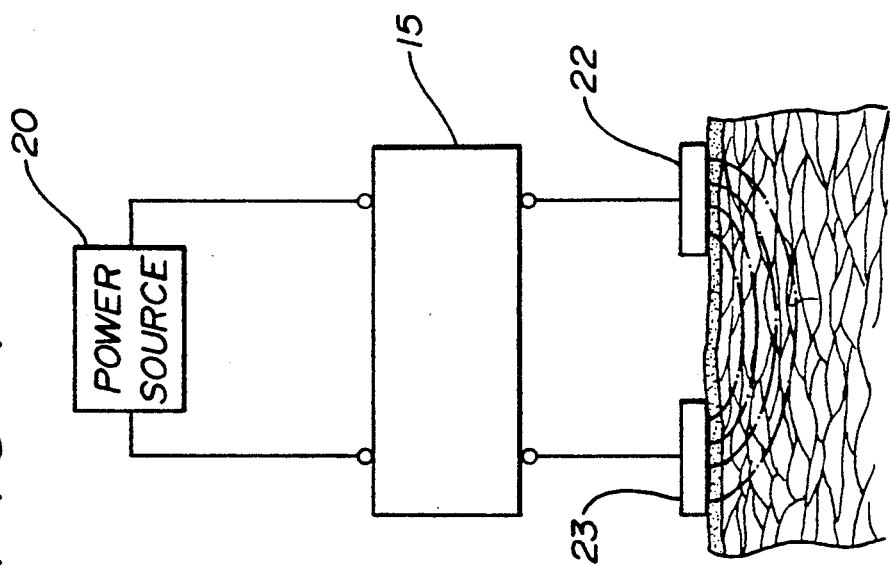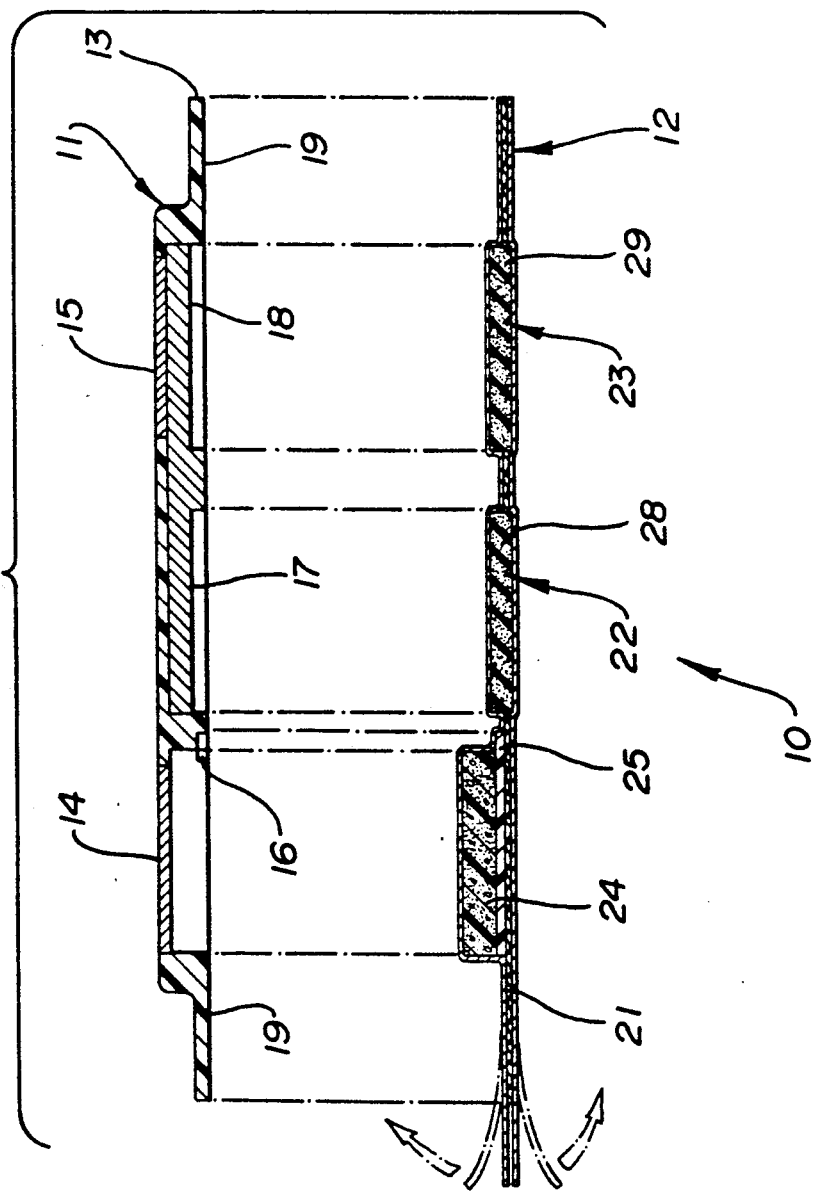

ELECTRICALLY ASSISTED TRANSDERMAL TRANSPORT DEVICE AND METHOD FOR RENEWING THE DEVICE

1. FIELD OF THE INVENTION

This invention relates to a means of recharging and remedicating a device for electrically assisted transport of molecules in solution, and more particularly, relates to replacing a consumable anode and its electrolyte portions of an air battery along with the solution of molecules to be transported in a disposable part of the device.

2. BACKGROUND

A power source is required in a device for electrically assisted transport and that is what distinguishes such a device from a passive transdermal delivery system. Therefore, the transport of molecules in solution in active transdermal delivery systems can be controlled. Many medications are better off supplied in a controlled manner according to the needs of the body based on clearance metabolism, serum levels, and the like.

Typically batteries have been applied as part of the power source circuit of transdermal delivery systems. Early systems had the battery as part of the electrodes; the use of a copper electrode on one side of the body and a zinc electrode on the other with electrolyte was proposed as the battery. In U S. Pat. Nos. 222,276 and 770,014 electrode battery combinations are explained. Battery current drives medication or a conducting salt into the body. The zinc and copper electrodes from the battery in the earlier patent has a concentric arrangement of electrodes; the other patent has electrodes with surfaces which project through separating insulation. The projections may have absorbent liquid containing pads placed between the projections and the body. Also various well-known primary cells have been use in electrically assisted transdermal transport systems, e.g. the commercial embodiment of the device disclosed in U.S. Pat. No. 4,141,359.

Another type of power source known but not applied to or disclosed for use in these systems is that shown in U.S. Pat. No. 3,436,270 wherein an air or oxygen cell for generating electrical energy is described. The cell includes a consumable metal anode and an air cathode. The anode is removable and replaceable, but this cell provides that the electrolyte has to be replaced and the removal of the electrolyte is a separate operation in the process of replacing the anode.

U.S. Pat. No. 3,531,327 discloses a liquid impermeable package containing a consumable metal anode and electrolyte for replenishing a mechanically rechargeable air cell. The anode may be a porous material impregnated with electrolyte or may be a solid anode packaged with electrolyte or a combination of the porous and solid anodes having a hydrophilic separator or matrix around the anode impregnated with an electrolyte. Any of those anodes can be packaged in a liquid impermeable bag. The package replaces a removed and discarded consumed anode and electrolyte.

External charging of these cells is not required as disclosed in U.S. Pat. No. 3,457,488 and there is no need to actively depolarize the cathode with a gas such as disclosed in U.S. Pat. No. 4,246,324. While cells which provide the advantage of quickly and easily being recharged by replacing the consumable anode and electrolyte are known, the concept of renewing an anode, electrolyte and active and indifferent reservoirs has not been applied to an electrically assisted transdermal transport system. A device for and method of redosing or medicating when recharging or reactivating the power source with an anode and electrolyte is unknown in devices for electrically assisted transdermal transport.

In the usual electrically assisted transdermal transport system, the power source is changed periodically. In acute applications, where the need may be for an hour or so of dosing, the active and indifferent reservoirs may be reused for some number of applications but still would be replaced after a few days. In chronic applications, the active and indifferent reservoirs would also be replaced after one or two days. Due to the rate of skin replacement, the longest possible period of continued use at one body location is about one week.

Also in the usual use of an electrically assisted transdermal transport system, the power source (battery) must be periodically replaced. In the conventional system, there is a trade-off between battery size (and hence device size), frequency of replacement and higher cost. Small devices are more desirable, but small devices require more frequent battery replacement and higher cost. Large devices are less desirable, but large devices need less frequent battery replacement and have lower cost. It is most likely that battery replacement and replacement of the reservoirs will occur on different schedules, making the use of the electrically assisted transdermal device more complicated than a passive transdermal patch.

The problem to be solved is how to replace the consumed parts of the active and indifferent reservoirs and the battery and how to adjust the relative amounts of the consumed constituents thereof so that they are consumed equally. The solution to those problems is addressed herein by an electrically assisted transdermal transport device of a minimal size. Since only the consumed parts of the battery are replaced, and since these are the low cost portions of the battery, the cost is low. Use of the device herein is simple and convenient since one replacement renews the battery and the active and indifferent reservoirs. Battery replacement is not a concern and battery life and capacity are not a constraint. For example, large dosage can be given because the battery capacity can be designed to satisfy the exact needs of the system used. Specifically, the higher currents needed for higher doses are possible since the battery does not need to last longer than the reservoirs.

SUMMARY OF THE INVENTION

The preferred invention is a device for electrically assisted transport of molecules into the skin. The device may have a renewable power source as part of a means for electrically assisted transport of molecules in solution through the skin of an animal. The device may have an anode and a battery electrolyte in fluid communication in a disposable part of the means for electrically assisted transport of molecules in solution. The device may have an air cathode on a reusable part of the means for electrically assisted transport so that when the reusable and disposable parts join, the battery electrolyte and the air cathode are in fluid communication. The power source is thereby renewed and electrically connected to the means for electrically assisted transport.

The means may have a reusable part which preferably includes a control in circuit for regulating the rate of electrically assisted transport and a support for attachment to the skin. An air cathode is most preferably associated with the support and is connected in circuit with the control. An anode contact is most preferably associated with the support and is connected in circuit with the control but otherwise is electrically isolated from the air cathode. A disposable part of the means may have a carrier shaped to conjugate with the support. An active reservoir system may contain the molecules in solution and is positioned on the carrier in circuit with and for contact with the animal skin. An indifferent reservoir system may contain an ion solution and is positioned on the carrier in circuit with and for contact with the animal skin. An anode on the carrier is most preferably in fluid communication with a battery electrolyte on the carrier. The anode and battery electrolyte are arranged on the carrier so that upon conjugation of the carrier and support the battery electrolyte and the air cathode are in fluid communication to renew a power source. The anode and the anode contact engage upon conjugation to place the power source in circuit for supplying power to control.

The support and the carrier may each be generally planar and one of which may have recesses to hold the anode, the active and indifferent reservoir systems and the battery electrolyte when the carrier and the support are conjugated. The air cathode preferably includes activated carbon on a conductive layer. The battery electrolyte is sandwiched between the activated carbon of the air cathode and the anode. The active reservoir system may contain an aqueous solution of the molecules in solution in a matrix. The indifferent reservoir system may contain the ion solution in a matrix. The ion solution preferably includes buffered saline above about 0.1 molar concentration. The battery electrolyte preferably includes saline solution above about 0.1 molar concentration with a pH of about 9 or above.

The ion solution may be contained in a matrix. The matrix may be a gel or a porous polymer. The molecules in solution or the ion solution may be contained in the matrix. The active reservoir system and indifferent reservoir system are spaced apart from one another in circuit and against the animal skin so the power source supplies energy through the control and an electric field is established through the animal skin. The carrier may have a separatable power source section so that the consumable portion of the power source can be independently renewed.

A method for renewing and replenishing a power source for a device for electrically assisted transport of molecules in solution may provide means for electrically assisted transport having a reusable part and a disposable part. The method preferably includes providing the reusable part with an air cathode and an anode contact on a support and providing the disposable part having an anode in fluid communication with a battery electrolyte on a carrier. The method renews the power source by joining the support and the carrier. The battery electrolyte, the air cathode and the anode are thus joined in fluid communication and the anode and the anode contact are electrically connected.

A method of providing a device for electrically assisted transport of molecules in solution may have the step of placing in a disposable part of the device for electrically assisted transport a battery electrolyte in fluid communication with an anode, an ion solution in an indifferent reservoir system and an aqueous solution of molecules in solution in an active reservoir system. The method connects an anode contact, an air cathode and a control in circuit in a reusable part of the electrically assisted device. The method joins the disposable and reusable parts so that the air cathode, the anode and the battery electrolyte combine in a power source. The anode engages the anode contact to connect the power source to the control and the aqueous solution in the active reservoir system and the ion solution in the indifferent reservoir system connect with the control to complete the electrically assisted transport device.

BRIEF DESCRIPTION OF THE DRAWINGS

FIG. 3 is a side view in cross section as would be seen along line 3—3 of FIG. 2.

FIG. 4 is a schematic diagram of the circuit of the control, power source and the active and indifferent reservoir systems as applied to the skin.

DETAILED DESCRIPTION OF THE DRAWINGS

Figure 1:
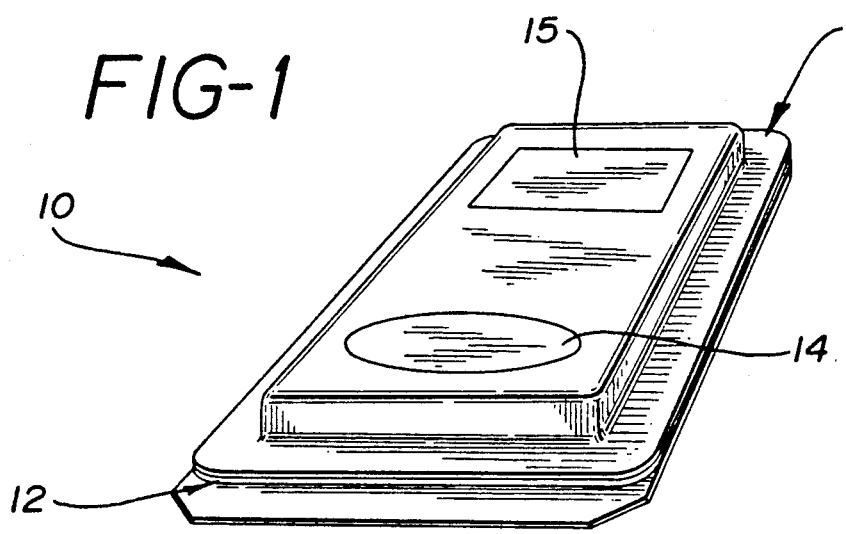
FIG. 1 is a perspective view of a preferred device for iontophoretic delivery of drugs to an animal.

While this invention is satisfied by embodiments in many different forms, there is shown in the drawings and will herein be described in detail, a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

FIG. 1 is a perspective view of the preferred embodiment of a device 10 for the electrically assisted transdermal transport of molecules in solution. Iontophoresis is one preferred form of transport for the delivery of drug into the skin of an animal. The preferred packaging of the present invention includes a reusable part 11 and a disposable part 12 which conjugate with one another to form the electrically assisted device 10 preferably for the active and controlled transdermal delivery of drug. The means for electrically assisted transdermal transport as used herein is broader than the preferred device 10 which will be described. Any electrically assisted transdermal transport is considered a part of this disclosure and the means for electrically assisted transport of molecules in solution through the skin of an animal is in the preferred form of the invention the reusable part 11.

The reusable part 11 has a support 13 to which is attached an air cathode 14, a control 15, an anode contact 16 and solution recessed 17 and 18. The support 13 is arranged with areas 19 for attachment to the disposable port 12. The control 15 regulates the flow of electric current to the electrically assisted transport device 10. The air cathode 14 is an unconsumed piece of an air battery power source 20. As used throughout this specification, the unconsumable piece of the electrically assisted device 10 is that which is not used up during transdermal transport of molecules in solution. Consequently, the reusable part 11 includes the unconsumed pieces of the electrically assisted device 10.

Figure 2:
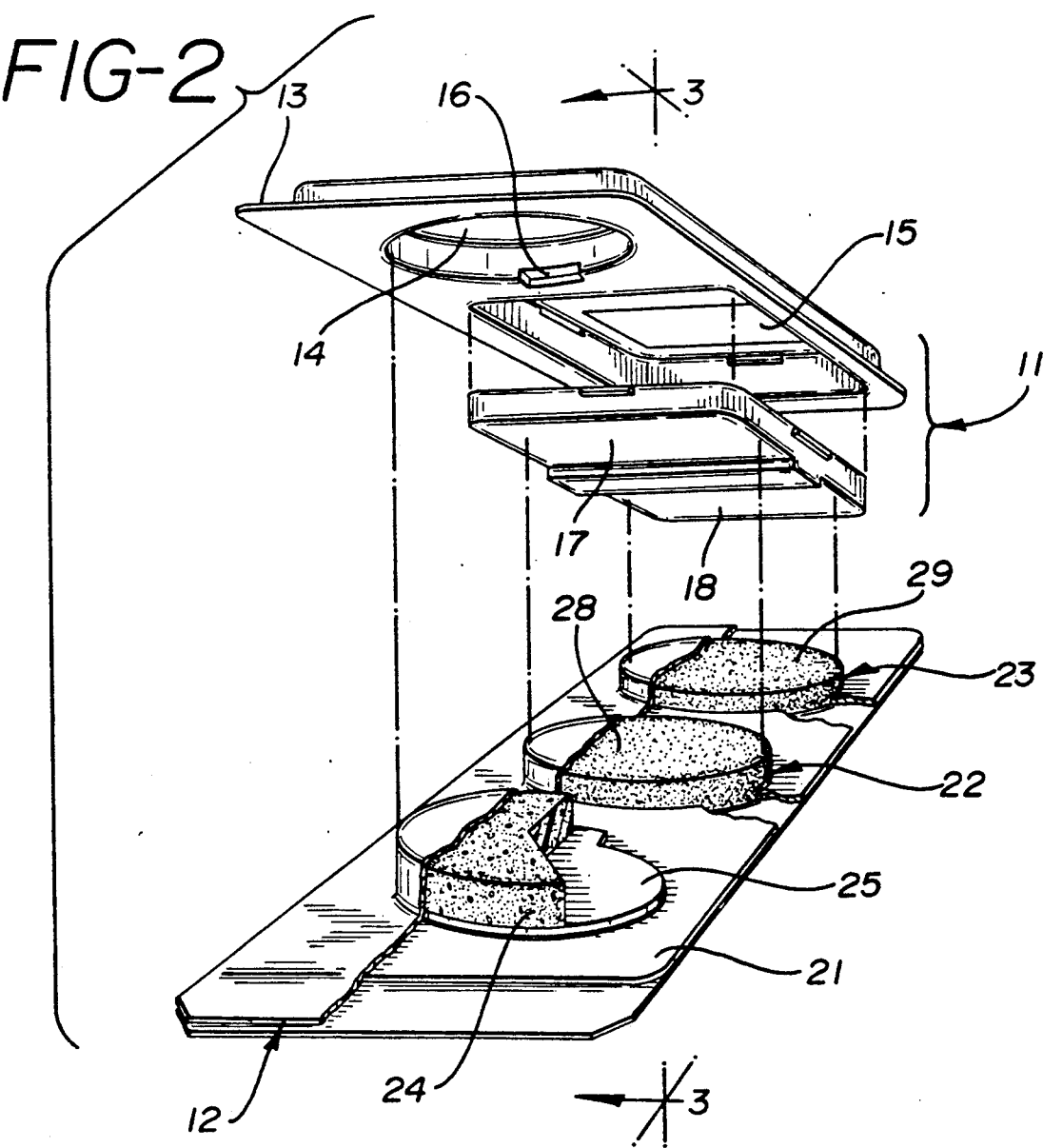
FIG. 2 is an exploded perspective view of the device of FIG. 1 wherein the parts of the iontophoretic delivery package are shown in their relative positions.

The disposable part 12 has the consumable pieces of the electrically assisted device 10 as shown in FIGS. 2 and 3. That is, the disposable part 12 has a carrier 21 which includes an active reservoir system 22, an indifferent reservoir system 23, a battery electrolyte 24 and an anode 25. The carrier 21 is shaped to conjugate with the support 13 for placing the anode 25 and anode contact 16 in circuit, for placing the electrolyte 24 of the power source 20 in fluid communication with the air cathode 14 to renew the air battery 20, and to position the active and indifferent reservoir systems 22 and 23 for contact with the skin of the animal upon application of the electrically assisted device 10. The active reservoir system 22 is supplied with molecules in solution for transport into the skin of the animal and as used herein the active reservoir system 22 includes the molecules in solution. The indifferent reservoir system 23 is supplied with an ion solution for aiding the transport of molecules in solution into the skin of the animal and as used herein the indifferent reservoir system 23 includes the ion solution.

The carrier 21 and support 13 are, as explained, shaped to conjugate when brought together so as to make physical interengagement and electrical connection. Specifically, the reusable and disposable parts 11 and 12 fit with one another, preferably and only in one way, such that the chemical, mechanical and electrical constituents of the electrically assisted device 10 are in communication with each other. The assembly is in the preferred device 10, by design of the shape of the reusable and disposable parts 11 and 12, arranged to conjugate in a particular way. The shape of the support and the carrier force 21 the preferred conjugation. The consumed pieces of the electrically assisted device 10 may thus be renewed by simply replacing the disposable part. The reusable part with the unconsumed pieces of the electrically assisted device is kept and never wears out. The economic efficiency of the aforesaid design allows the reusable part 11 to be made of expensive and reliable components since it is only purchased once. The disposable part 12 is, on the other hand, made by a high speed process with low cost materials so as to provide a cost effective assembly of the preferred electrically assisted device 10.

The conjugation of the carrier 21 and support 13 brings the parts 11 and 12 of the device 10 together and connects the power source 20 in circuit with the control 15. The air cathode 14 of the preferred power source 20 is made of activated carbon and is part of the support 13 as shown in FIG. 3. The consumed pieces of the power source 20 are the battery electrolyte 24 and the anode 25 on the carrier 21. When the support 13 and carrier 21 are conjugated the power source 20 is constructed, renewed and placed in circuit.

The active and indifferent reservoir systems 22 and 23 are positioned on the carrier 21 so that when conjugated with the support 13 they are in circuit with the control 15 for the electrical assistance of the transport of the molecules in solution into the skin of the animal. The active and indifferent reservoir systems 22 and 23 are positioned on the carrier 21 so that they are exposed to the skin of the animal when the electrically assisted device 10 is applied thereto. The support 13 includes in circuit and specifically in series the active reservoir system 22, the control 15 and the indifferent reservoir system 23 as best seen in FIGS. 2 and 3. The way in which those components are in circuit is best understood by examination of FIG. 4 a schematic diagram.

To complete the circuit the application of the active and indifferent reservoir systems 22 and 23 to the skin of the animal enables the transport of the molecules in solution through the skin. The active and indifferent reservoir systems 22 and 23 are on the carrier 21 so that they are spaced apart from one another to establish an electric field 27 through the skin when applied as mentioned.

The materials of the preferred electrically assisted device 10 are selected to accomplish the intended functions. In particular, the support 13 and carrier 21 are preferably a polymer formed or molded as required to facilitate the conjugation and the attachment to the various consumed and unconsumed pieces and to the skin of the animal. The active and indifferent reservoir systems 22 and 23 are shown in the preferred electrically assisted device as shown in FIGS. 1, 2 and 3, and are made of a matrix 28 and 29 respectively, such as a porous polymer. The porous polymer may contain the molecules in solution or an ion solution as required for the active or indifferent reservoir systems 22 and 23. A gel can be used in place of the porous polymer as the matrix 28 and 29. Fluid, as used herein, is not to be limited to its definition as either a liquid, a gas or combination thereof. As used herein, fluid includes that which may be encompassed by matrix.

A method for renewing and replenishing an electrically assisted device 10 for transport of molecules in solution includes the step of providing the reusable part 11 with the air cathode 14 and the control 15 in circuit and on the support 13. The method has the step of placing the anode contact 16 in an exposed position on the support 13 and in circuit but otherwise electrically isolated from the air cathode 14. The method then has the step of providing the disposable part 12 on the carrier 21. The disposable part 12 has the active reservoir system 22 with the molecules in solution to be passed, the indifferent reservoir system 23 with the ion solution for contact with the animal skin and the anode 25 in fluid communication with the battery electrolyte 24. The method includes the step of joining the reusable and disposable parts 11 and 12 to form the power source 20 by causing fluid communication of the battery electrolyte 24 sandwiched between the air cathode 14 and the anode 25. Thus the anode contact 16, the anode 25, electrolyte 24, and the air cathode 14 are in circuit to supply electrical power to the control 15, and the active reservoir system 22, the indifferent reservoir system 23, the control 15, and the skin of the animal are in circuit for electrically assisted transport of the molecules in solution into the skin of the animal.

A method of providing an electrically assisted device 10 for transport of molecules in solution includes placing in the disposable part 12 of the electrically assisted device 10, the battery electrolyte 24 in fluid communication with the anode 25, the ion solution in the indifferent reservoir system 23 and the aqueous solution of molecules in solution in an active reservoir system 22. The steps of placing in the reusable part 11 of the electrically assisted device 10 the anode contact 16, the air cathode 14 and the control 15 in circuit in the reusable part 11 of the electrically assisted device 10 and joining the disposable and reusable parts 11 and 12 so that the air cathode 14, battery electrolyte 24 and anode 25 combine in the power source 20 and the aqueous solution in the active reservoir system 22, the ion solution in an indifferent reservoir system 23 connect with control 15 to complete the electrically assisted device 10.

What is claimed is:

1. A renewable power source as a portion of a device for electrically assisted transport of molecules into the skin comprising:

a means for electrically assisted transport of molecules in solution through the skin of an animal;

an anode and a battery electrolyte in fluid communication in a disposable part the means for electrically assisted transport of molecules in solution;

an air cathode on a reusable part of the means for electrically assisted transport so that when the reusable and disposable parts join, the battery electrolyte and the air cathode are in fluid communication thus renewing the power source and the power source is electrically connected to the means for electrically assisted transport.

2. A device for electrically assisted transport of molecules through the skin of an animal comprising:

a reusable part including a control in circuit for regulating the rate of electrically assisted transport and a support for attachment to the disposable part;

an air cathode associated with the support and connected in circuit with the control;

an anode contact associated with the support and connected in circuit but otherwise electrically isolated from the air cathode;

a disposable part having a carrier shaped to conjugate with the support;

an active reservoir system supplied with the molecules in solution, positioned on the carrier in circuit and for contact with the animal skin;

an indifferent reservoir system supplied with an ion solution, positioned on the carrier in circuit for contact with the animal skin, and an anode in fluid communication with a battery electrolyte, the anode and battery electrolyte associated with the disposable part and arranged on the carrier so that upon conjugation of the carrier and support the battery electrolyte and the air cathode are in fluid communication to renew a power source, the anode and the anode contact engage to place the power source in circuit for supplying power to control.

3. The device of claim 2 wherein the support and the carrier are each generally planar and one of which has recesses to hold the anode, the active and indifferent reservoir systems and the battery electrolyte when the carrier and the support are conjugate.

4. The device of claim 3 wherein the indifferent reservoir system contains the ion solution in a matrix.

5. The device of claim 4 wherein the ion solution includes a buffered saline above about 0.1 molar concentration.

6. The device of claim 4 wherein the battery electrolyte includes a saline solution above about 0.1 molar concentration with a pH of about 9 or above.

7. The device of claim 2 wherein the air cathode includes activated carbon on a conductive layer.

8. The device of claim 7 wherein the battery electrolyte is in a sandwich between the activated carbon of the air cathode and the anode.

9. The device of claim 2 wherein the active reservoir system contains an aqueous solution of the molecules in solution in a matrix.

10. The device of claim 2 wherein the ion solution is contained in a matrix.

11. The device of claim 10 wherein the matrix is a gel.

12. The device of claim 10 wherein the matrix is a porous polymer.

13. The device of claim 2 wherein the molecules in solution is contained in a matrix.

14. The device of claim 13 wherein the matrix is a gel.

15. The device of claim 13 wherein the matrix is a porous polymer.

16. The device of claim 2 wherein the active reservoir system and indifferent reservoir system are spaced apart from one another in circuit and against the animal skin so the power source supplies energy through the control and an electric field is established through the animal skin between the active and indifferent electrically assisted systems.

17. The device of claim 2 wherein the carrier has a separatable power source section so that the consumable portion of the power source can be independently renewed.

18. A method for renewing and replenishing a power source for a device for electrically assisted transport of molecules in solution including the following steps:

providing means for electrically assisted transport having a reusable part and a disposable part;

providing the reusable part with an air cathode and an anode contact on a support;

providing the disposable part having an anode in fluid communication with a battery electrolyte on a carrier;

renewing the power source by joining the support and the carrier, so that the battery electrolyte, the air cathode and the anode are in fluid communication, and electrically connecting the anode with the anode contact by joining the support and the carrier.

19. A method of providing a device for electrically assisted transport of molecules in solution having the steps of:

placing in a disposable part of the device for electrically assisted transport a battery electrolyte in fluid communication with an anode, an ion solution in an indifferent reservoir system and an aqueous solution of molecules in solution in an active reservoir system;

connecting an anode contact, an air cathode and a control in circuit in a reusable part of the electrically assisted device, and joining the disposable and reusable parts so that the air cathode, the anode and the battery electrolyte combine in a power source, the anode engages the anode contact to connect the power source to the control, and the aqueous solution in the active reservoir system and the ion solution in the indifferent reservoir system connect with the control to complete the electrically assisted transport device.

* * * * *

UNITED STATES PATENT AND TRADEMARK OFFICE
CERTIFICATE OF CORRECTION

PATENT NO. : 5,037,381
DATED : August 6, 1991
INVENTOR(S) : C. Randolph Bock; Burton H. Sage, Jr.

It is certified that error appears in the above-identified patent and that said Letters Patent is hereby corrected as shown below:

On The Title Page:   Item [73]

Assignee should read   Becton, Dickinson and Company, Franklin Lakes, New Jersey COLUMN 7 and 8;
Claim 7, line 1, "2" should be --1--.
Claim 4, line 1, "3" should be --2--.
Claim 16, lines 6 and 7 , it reads "electrically assisted" whereas it should read --reservoir--.

Signed and Sealed this

Tenth Day of November, 1992

Attest:

DOUGLAS B. COMER

*Attesting Officer*   Acting Commissioner of Patents and Trademarks